(12) United States Patent
Beavis et al.

(10) Patent No.: US 9,550,033 B2
(45) Date of Patent: *Jan. 24, 2017

(54) METERING SYSTEM AND METHOD FOR FLUID DELIVERY

(71) Applicant: DEKA Products Limited Partnership, Manchester, NH (US)

(72) Inventors: Russell H. Beavis, Merrimack, NH (US); Larry B. Gray, Merrimack, NH (US); Derek G. Kane, Manchester, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/799,054

(22) Filed: Jul. 14, 2015

(65) Prior Publication Data

US 2015/0316405 A1 Nov. 5, 2015

Related U.S. Application Data

(63) Continuation of application No. 13/968,710, filed on Aug. 16, 2013, which is a continuation of application (Continued)

(51) Int. Cl.
*A61M 11/00* (2006.01)
*A61M 15/00* (2006.01)
(Continued)

(52) U.S. Cl.
CPC ..... *A61M 15/0068* (2014.02); *A61M 15/0003* (2014.02); *A61M 15/008* (2014.02);
(Continued)

(58) Field of Classification Search
CPC .............. A61M 15/0068; A61M 15/0066; A61M 15/0003; A61M 15/0048; A61M 15/008; A61M 15/0065; A61M 15/0045; A61M 15/0085; A61M 2205/3368; A61M 2205/3379; A61M 2016/0021; A61M 2205/3375; A61M 2202/03; A61M 2016/0039; G01H 3/00; G01F 1/007; G01F 22/00; G01F 23/14; G01F 17/00; G10K 9/04; B05B 12/085
(Continued)

(56) References Cited

U.S. PATENT DOCUMENTS

| 3,915,171 A | 10/1975 | Shermeta |
| 3,990,797 A | 11/1976 | Neukermans et al. |

(Continued)

FOREIGN PATENT DOCUMENTS

| EP | 0209677 B1 | 7/1990 |
| EP | 0816677 B1 | 9/2003 |

(Continued)

OTHER PUBLICATIONS

Gebhart et al., "A New Device for Aerosol and Gas Inhalation Studies and Its Application in Lung Investigations", Journal of Aerosol Science, vol. 11, No. 3, pp. 237-238, 1980.
(Continued)

*Primary Examiner* — Steven Douglas
(74) *Attorney, Agent, or Firm* — Michael George Norris

(57) ABSTRACT

An apparatus for metering the delivery of an aerosol. The apparatus has a variable acoustic source and a microphone, both acoustically coupled to a volume having a fluid region and an air region. The apparatus may also include a processor to determine a volume of the air region based on signals received from the microphone and the variable acoustic source. A fluid valve is coupled to the processor, and is configured to allow an amount of fluid to exit the fluid region associated with the volume of the air region. An atomizer,
(Continued)

coupled to the fluid region, is configured to aerosolize at least a portion of the fluid.

36 Claims, 16 Drawing Sheets

Related U.S. Application Data

No. 12/897,100, filed on Oct. 4, 2010, now Pat. No. 8,511,299, which is a continuation of application No. 11/942,883, filed on Nov. 20, 2007, now Pat. No. 7,806,116, which is a continuation of application No. 10/670,641, filed on Sep. 25, 2003, now Pat. No. 7,305,984.

(51) Int. Cl.
| | |
|---|---|
| B05B 12/08 | (2006.01) |
| G01F 17/00 | (2006.01) |
| G01F 22/00 | (2006.01) |
| G01F 23/14 | (2006.01) |
| G10K 9/04 | (2006.01) |
| G01F 1/00 | (2006.01) |
| G01H 3/00 | (2006.01) |
| A61M 16/00 | (2006.01) |

(52) U.S. Cl.
CPC .... *A61M 15/0045* (2013.01); *A61M 15/0048* (2014.02); *A61M 15/0065* (2013.01); *A61M 15/0066* (2014.02); *A61M 15/0085* (2013.01); *B05B 12/085* (2013.01); *G01F 1/007* (2013.01); *G01F 17/00* (2013.01); *G01F 22/00* (2013.01); *G01F 23/14* (2013.01); *G01H 3/00* (2013.01); *G10K 9/04* (2013.01); *A61M 2016/0021* (2013.01); *A61M 2016/0039* (2013.01); *A61M 2202/03* (2013.01); *A61M 2205/3368* (2013.01); *A61M 2205/3375* (2013.01); *A61M 2205/3379* (2013.01)

(58) Field of Classification Search
USPC ............ 128/200.14, 200.18, 200.21, 200.22, 128/203.12, 203.14, 205.23, 205.24, 128/203.26, 200.16; 73/149, 649, 290 B; 137/565.01, 565.34; 261/27
See application file for complete search history.

(56) References Cited

U.S. PATENT DOCUMENTS

| | | | |
|---|---|---|---|
| 4,370,986 A | 2/1983 | Gebhart et al. | |
| 4,453,523 A | 6/1984 | Poehlman | |
| 4,474,061 A | 10/1984 | Parker | |
| 4,484,577 A | 11/1984 | Sackner et al. | |
| 4,734,092 A | 3/1988 | Millerd | |
| 4,811,595 A | 3/1989 | Marciniak et al. | |
| 4,991,433 A * | 2/1991 | Warnaka ................. | G01F 17/00 367/908 |
| 5,156,776 A | 10/1992 | Loedding et al. | |
| 5,349,852 A | 9/1994 | Kamen et al. | |
| 5,429,605 A | 7/1995 | Richling et al. | |
| 5,439,444 A | 8/1995 | Anderson et al. | |
| 5,443,059 A | 8/1995 | Koch et al. | |
| 5,522,385 A | 6/1996 | Lloyd et al. | |
| 5,526,844 A | 6/1996 | Kamen et al. | |
| 5,533,389 A | 7/1996 | Kamen et al. | |
| 5,575,310 A | 11/1996 | Kamen et al. | |
| 5,641,892 A | 6/1997 | Larkins et al. | |
| 5,704,520 A | 1/1998 | Gross | |
| 5,811,659 A | 9/1998 | Giebler | |
| 5,842,468 A | 12/1998 | Denyer et al. | |
| 5,884,620 A | 3/1999 | Gonda et al. | |
| 5,887,586 A | 3/1999 | Dahlback et al. | |
| 5,906,202 A | 5/1999 | Schuster et al. | |
| 5,957,124 A | 9/1999 | Lloyd et al. | |
| 5,997,546 A | 12/1999 | Foster et al. | |
| 6,008,468 A | 12/1999 | Tanaka et al. | |
| 6,026,808 A | 2/2000 | Armer et al. | |
| 6,085,740 A * | 7/2000 | Ivri ..................... | A61M 11/005 128/200.14 |
| 6,095,141 A | 8/2000 | Armer et al. | |
| 6,119,684 A | 9/2000 | Noehl et al. | |
| 6,167,880 B1 | 1/2001 | Gonda et al. | |
| 6,192,882 B1 | 2/2001 | Gonda | |
| 6,208,107 B1 | 3/2001 | Maske et al. | |
| 6,264,631 B1 | 7/2001 | Willis et al. | |
| 6,321,597 B1 | 11/2001 | Demers et al. | |
| 6,349,719 B2 | 2/2002 | Gonda | |
| 6,467,476 B1 | 10/2002 | Ivri et al. | |
| 6,506,179 B1 | 1/2003 | Tiefenthal et al. | |
| 6,589,229 B1 | 7/2003 | Connelly et al. | |
| 6,669,669 B2 | 12/2003 | Flaherty et al. | |
| 6,692,457 B2 | 2/2004 | Flaherty et al. | |
| 6,699,218 B2 | 3/2004 | Flaherty et al. | |
| 6,702,779 B2 | 3/2004 | Connelly et al. | |
| 6,723,072 B2 | 4/2004 | Flaherty et al. | |
| 6,740,059 B2 | 5/2004 | Flaherty | |
| 6,808,369 B2 | 10/2004 | Gray et al. | |
| 6,830,558 B2 | 12/2004 | Flaherty et al. | |
| 6,939,324 B2 | 9/2005 | Gonnelli et al. | |
| 7,083,719 B2 | 8/2006 | Bowman, Jr. et al. | |
| 7,305,984 B2 | 12/2007 | Altobelli et al. | |
| 7,806,116 B2 | 10/2010 | Altobelli et al. | |
| 8,511,299 B2 * | 8/2013 | Altobelli ........... | A61M 15/0045 128/200.14 |
| 2002/0022798 A1 | 2/2002 | Connelly et al. | |
| 2002/0033173 A1 | 3/2002 | Shofner et al. | |
| 2002/0072733 A1 | 6/2002 | Flaherty | |
| 2002/0073952 A1 | 6/2002 | Liu et al. | |
| 2002/0153006 A1 | 10/2002 | Zimlich, Jr. et al. | |
| 2003/0146300 A1 | 8/2003 | Denyer et al. | |
| 2003/0220598 A1 | 11/2003 | Busby et al. | |
| 2004/0015131 A1 | 1/2004 | Flaherty et al. | |
| 2004/0046137 A1 | 3/2004 | Herbert et al. | |
| 2004/0106899 A1 | 6/2004 | McMichael et al. | |
| 2004/0147874 A1 | 7/2004 | Kliem et al. | |
| 2007/0088259 A1 | 4/2007 | Chu et al. | |

FOREIGN PATENT DOCUMENTS

| | | |
|---|---|---|
| EP | 0724889 B1 | 4/2004 |
| GB | 2053378 A | 2/1981 |
| RU | 2240142 C2 | 11/2004 |
| SU | 1131285 A1 | 4/1995 |
| WO | WO 85/05657 A1 | 12/1985 |
| WO | WO 93/23096 A1 | 11/1993 |
| WO | WO 96/41156 A1 | 12/1996 |
| WO | WO 98/48873 A1 | 11/1998 |
| WO | WO 99/37347 A1 | 7/1999 |
| WO | WO 01/58514 A1 | 8/2001 |

OTHER PUBLICATIONS

Gebhart et al., "*Individual Aerosol Exposure Unit for Small Rodents Using Photometry*", Journal of Aerosol Science, vol. 19, No. 7, pp. 1105-1108, 1988.

Heyder et al. "*Experimental Studies of the Total Deposition of Aerosol Particles in the Human Respiratory Tract*", Journal of Aerosol Science, vol. 4, pp. 191-208, 1973.

"*RAP—Today's Most Sensitive System for Monitoring Lung Emphysema,*" Respiratory Aerosol Probe: Jan. 19, 2004, http://www.inamed.de/EN/main/02 produkte/05 rap.htm: pp. 1-2.

European Search Report dated Jun. 9, 2010, received in European patent application No. 04785145.6-1268, 4 pgs.

European Search Report dated Mar. 29, 2011, received in European patent application No. 10183339.0-1268/2269743, 7 pgs.

European Search Report dated Jun. 20, 2011, received in European patent application No. 10183347.3-1268, 4 pgs.

(56) References Cited

OTHER PUBLICATIONS

International Preliminary Report on Patentability dated Sep. 18, 2007, received in International application No. PCT/US2004/031672, 12 pgs.
European Search Report dated Aug. 6, 2015, received in European patent application No. 12183108.
Office Action dated May 13, 2013, received in Russian patent application No. 2010132226, 8 pgs. *Translation Included*.
Office Action date Mar. 5, 2013, received in Japanese patent application No. 2010-540955, 10pgs *Translation Included*.
Office Action dated Feb. 20, 2014, received in Japanese patent application No. 2010540955, 10pgs *Translation Included*.
International Search Report and Written Opinion date Mar. 7, 2013, received in International application No. PCT/US2012/071280, 13 pgs.
U.S. Appl. No. 12/897,100, B9-B12 and C1-C7.
Office Action dated Feb. 20, 2014, received in Japanese patent application No. 2010-540955, 10pgs Translation Included.

* cited by examiner

FIG. 1

METERING SYSTEM AND METHOD FOR FLUID DELIVERY

RELATED APPLICATIONS

The present application is a Continuation of U.S. patent application Ser. No. 13/968,710, filed Aug. 16, 2013 and entitled "Metering System and Methods for Aerosol Delivery," which is a Continuation of application of U.S. patent application Ser. No. 12/897,100, filed Oct. 4, 2010 and entitled "Metering System and Method for Aerosol Delivery", now U.S. Pat. No. 8,511,299, issued Aug. 20, 2013, which is a Continuation application of U.S. patent application Ser. No. 11/942,883, filed Nov. 20, 2007 and entitled "Method System and Method for Aerosol Delivery", now U.S. Pat. No. 7,806,116, issued Oct. 5, 2010, which is a Continuation of U.S. patent application Ser. No. 10/670,641, filed Sep. 25, 2003 and entitled "Metering System and Method for Aerosol Delivery", now U.S. Pat. No. 7,305,984, issued Dec. 11, 2007, all of which are hereby incorporated herein by reference in their entireties.

Additionally, the present application contains subject matter related to that of U.S. patent application Ser. No. 10/675,278, filed Sep. 30, 2003 and entitled "Detection System and Method for Aerosol Delivery", now U.S. Pat. No. 7,342,660, issued Mar. 11, 2008; U.S. patent application Ser. No. 10/670,977, filed Sep. 25, 2003 and entitled "System and Method for Improved Volume Measurement," now U.S. Pat. No. 7,066,029, issued Jun. 27, 2006; U.S. patent application Ser. No. 10/671,278, filed Sep. 25, 2003 and entitled "System and Method for Aerosol Delivery," now U.S. Pat. No. 7,021,560, issued Apr. 4, 2006; and U.S. patent application Ser. No. 10/670,924, filed Sep. 25, 2003 and entitled "Valve System and Method for Aerosol Drug Delivery," now U.S. Pat. No. 7,146,977, issued Dec. 12, 2006. The disclosures of the foregoing are incorporated herein by reference.

FIELD OF THE INVENTION

The present invention generally relates to systems and methods for metering and outputting quantities of aerosolized substances. More particularly, embodiments of the present invention can relate to systems and methods for accurately delivering atomized drugs.

BACKGROUND

Aerosolized drugs for inhalation are considered reasonable alternatives to injections or other types of drug-delivery systems, such as intravenous delivery, subcutaneous injection, and intra-muscular. For example, insulin can be delivered by inhaling an aerosolized form, thus sparing a patient pain and inconvenience caused by subcutaneous injection of insulin.

Inhaling aerosols, however, typically lacks the accuracy of injections, and so is inappropriate for use in situations where accurate dosing is critical. With aerosolized drugs, the proper amount required for delivery is often not properly metered for delivery. For example, asthma inhalers typically have an acceptable accuracy of plus or minus 25% of the nominal dose. For systemic drug delivery of insulin, on the other hand, such a level of accuracy is considered too unpredictable to allow for appropriate use, even though aerosolized delivery is much less harmful to a patient than intravenous delivery.

Thus, a need exists for accurately and predictably delivering a predetermined dose of aerosolized drugs.

SUMMARY OF THE INVENTION

An embodiment comprises a variable acoustic source and a microphone, both acoustically coupled to a volume that is divided into an air region and a fluid region. A processor is configured to receive a signal from the microphone, and to determine a volume of the air region. A fluid valve is configured to allow an amount of fluid to exit the fluid region, the amount of fluid being associated with the volume of the air region. An atomizer is coupled to the fluid region, and is configured to aerosolize at least a portion of the amount of fluid.

BRIEF DESCRIPTION OF THE DRAWINGS

FIG. 1 is a schematic diagram of a system for outputting an aerosol, according to an embodiment of the invention.

DETAILED DESCRIPTION

Figure 1:
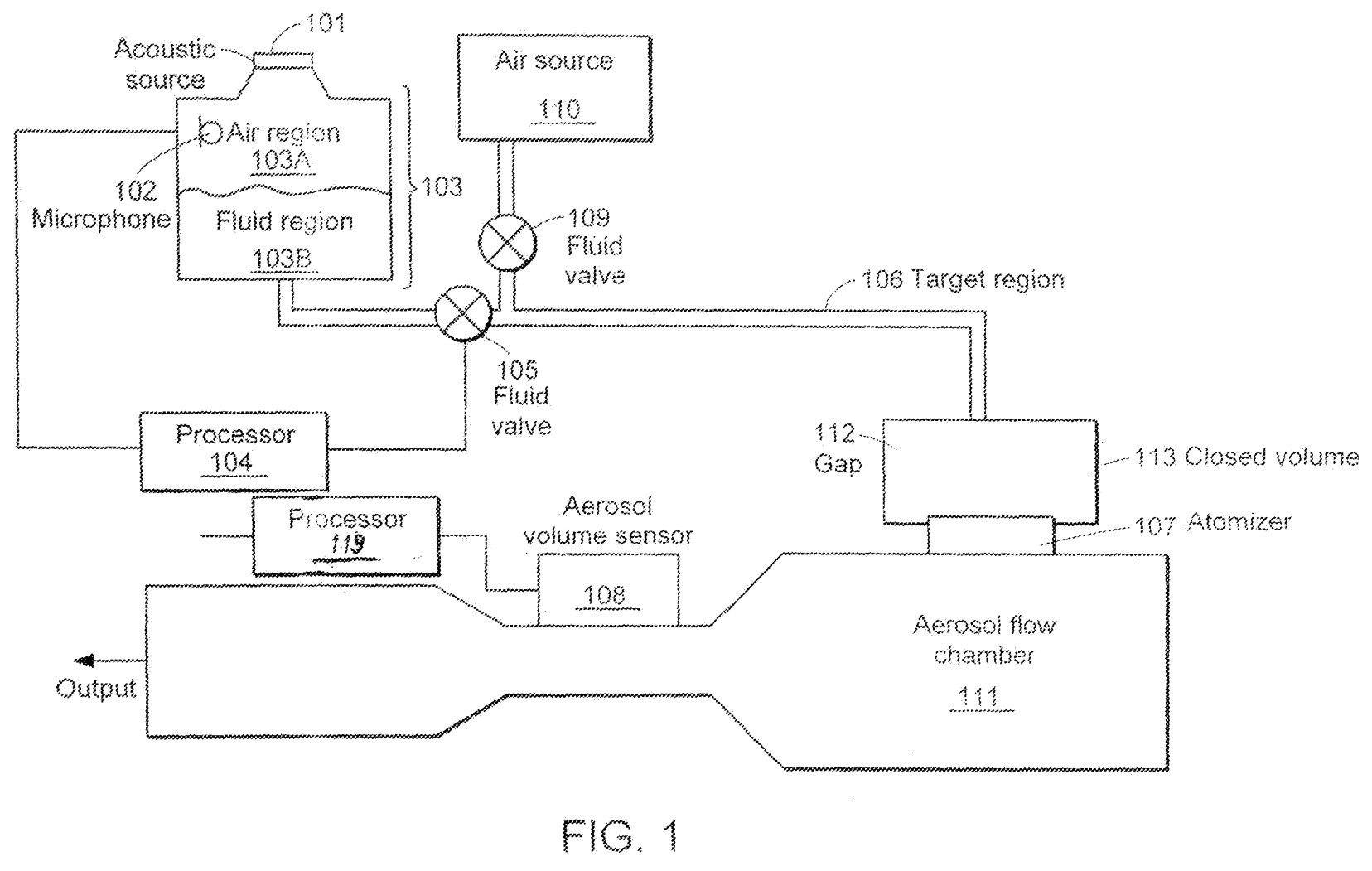
Figure 2:
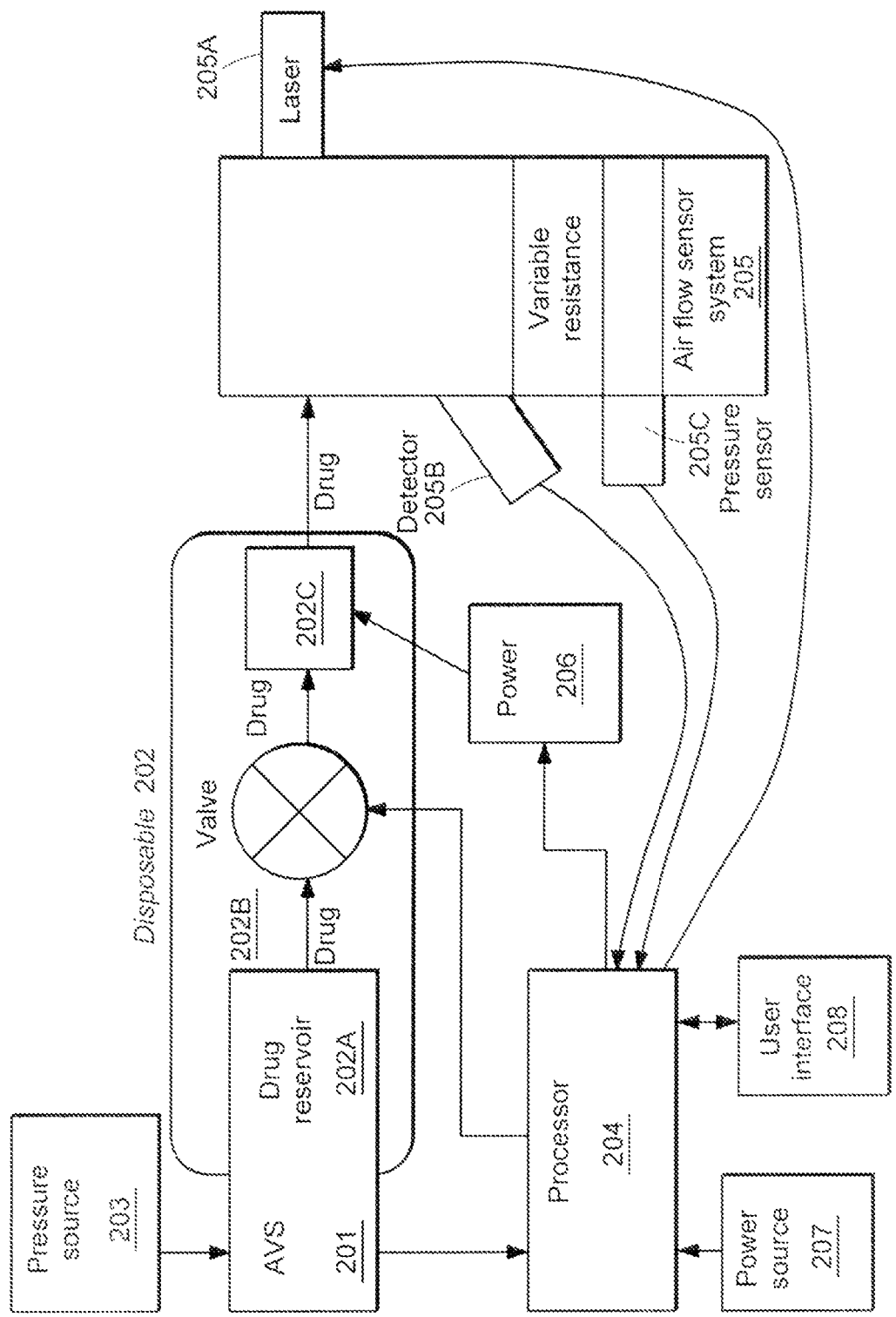
FIG. 2 is a schematic diagram of a system for outputting an aerosol, according to an embodiment of the invention in the context of aerosolized drug delivery.

Embodiments of the invention include systems and methods for outputting an aerosol. For purposes of this application, the term aerosol includes airflows containing particles, such as aerosolized liquids, powders, and combinations of the two. FIG. 1 displays a schematic overview of a system for outputting an aerosol, according to an embodiment of the invention. In this embodiment, variable acoustic source 101 and microphone 102 are acoustically coupled to chamber 103. Volume 103 is divided into air region 103a and fluid region 103b. For purposes of this application, the term air includes any gas or combination of gases.

Processor 104 is configured to receive a signal from microphone 102, and to determine a volume of air region 103a. Processor 104 is in communication with fluid valve 105, and is configured to send a control signal to fluid valve 105 to open and close fluid valve 105 to allow an amount of fluid out from fluid region 103b into target region 106. The amount of fluid released into target region 106 is associated with the determined volume of air region 103a. In one embodiment, chamber 103 is a fixed volume, and so the volume of fluid released into target region 106 is substantially identical to a determined change in volume of air region 103a. Target region 106 is coupled to atomizer 107, which is configured to aerosolize at least a portion of the fluid that has exited fluid region 103b.

In one embodiment, the system includes a second processor 119 that is configured to calculate a volume of the aerosolized fluid, and is further configured to output a volume signal associated with the calculated volume. In this embodiment, the amount of fluid allowed to enter target region 106 is associated both with the volume of air region 103a and with the aerosol volume.

The second processor is configured to receive a signal from volume sensor 108 in communication with aerosol flow chamber 111. Volume sensor 108 can be any combination of hardware and software configured to collect information for determining aerosol volume. For the purposes of the invention, the terms pressure, air flow and flow rate are all used interchangeably, depending on the context.

The second processor is not shown in FIG. 1, and for the purposes of the invention, processor 104 and the second processor can be the same processor, or can be separate from each other. For the purposes of the invention, the term processor includes, for example, any combination of hardware, computer programs, software, firmware and digital logical processors capable of processing input, executing algorithms, and generating output as necessary to practice embodiments of the present invention. The term processor can include any combination of such processors, and may include a microprocessor, an Application Specific Integrated Circuit (ASIC), and state machines. Such a processor can include, or can be in communication with, a processor readable medium that stores instructions that, when executed by the processor, causes the processor to perform the steps described herein as carried out, or assisted, by a processor.

For the purposes of the invention, "processor readable medium," or simply "medium," includes but is not limited to, electronic, optical, magnetic, or other storage or transmission devices capable of providing a processor with processor readable instructions. Other examples of suitable media include, but are not limited to, a floppy disk, CD-ROM, magnetic disk, memory chip, ROM, RAM, ASIC, configured processor, all optical media, all magnetic tape or other magnetic media, or any other medium from which a processor can read. Also, various other forms of processor readable media may transmit or carry instructions to a computer, including a router, private or public network, or other transmission device or channel. Also, various other forms of processor readable media may transmit or carry instructions to a computer, including a router, private or public network, or other transmission device or channel.

Target region 106 is coupled to air valve 109 and air source 110. Processor 104 can be further configured to send a control signal to air valve 109 to open and close air valve 109, thereby selectively exposing air source 110 to target region 106 and to atomizer 107. Air source 110 can be a compressed air source or liquefied air source, an air source open to the atmosphere, or any air source useful for moving fluid from target region 106 to atomizer 107, and/or for purging target region 106. In one alternative embodiment, air source 110 may comprise a volume containing an amount of liquefied propellant gas, where air valve 109 is configured in such a way as to connect to the portion of the volume typically containing vapor.

In one preferred embodiment, air source 110 is connected to target region 106 through air valve 109 in close proximity to fluid valve 105. Thus, when air valve 109 is opened, air from air source 110 will push a substantial portion of the volume of fluid in target region 106 toward the physical gap 112 in closed volume 113 and then to atomizer 107. Additionally, if the internal diameter of target region 106 is comparatively narrow, such as in a small bore capillary, utilizing air from air source 110 to push the volume of fluid in target region 106 toward atomizer 107 may have the additional advantages of reducing or eliminating blockage of the system, such as crystal growth, and biological contamination that could result from fluid remaining otherwise remain in target region 106 and improving accuracy of the system by ensuring that a substantial portion of the fluid exits target region 106 toward atomizer 107.

FIG. 2 is a schematic diagram of a system for outputting an aerosol, according to an embodiment of the invention, in the context of aerosolized drug delivery. In this embodiment, acoustic volume sensor 201 is coupled to disposable drug cassette 202. Pressure source 203 is coupled to acoustic volume sensor 201 to assist in outputting the drug from acoustic volume sensor 201 to disposable cassette 202. Disposable cassette 202 includes drug reservoir 202a, valve 202b and atomizer 202c, and is detachably coupled to acoustic volume sensor 201. Atomizer 202c can be, for example, an electro-hydrodynamic atomizer. Processor 204 is coupled to acoustic volume sensor 201 to calculate an amount of drug to output from drug reservoir 202a, and to control valve 202b.

Atomizer 202c is coupled to air flow sensor system 205. Air flow sensor system 205 can be any known system for measuring air flow or pressure of the aerosolized drug to be output to a patient. For example, air flow sensor system 205 can include an anemometer, a pin-wheel sensor, or any other sensor operable to measure air flow, flow rate or pressure. In the embodiment shown, air flow sensor system 205 is a light scatter detection system that includes light source 205a, light detector 205b, and pressure sensor 205c. Processor 204 is coupled to light source 205a, light detector 205b and pressure sensor 205c. Processor 204 is configured to receive a light detection signal 205b and pressure or air flow signal from pressure sensor 205c, and calculate the aerosol volume inside air flow sensor system 205. As stated above, this system is described in detail in U.S. patent application Ser. No. 10/670,655, titled "Detection System and Method for Aerosol Delivery."

Figure 3:
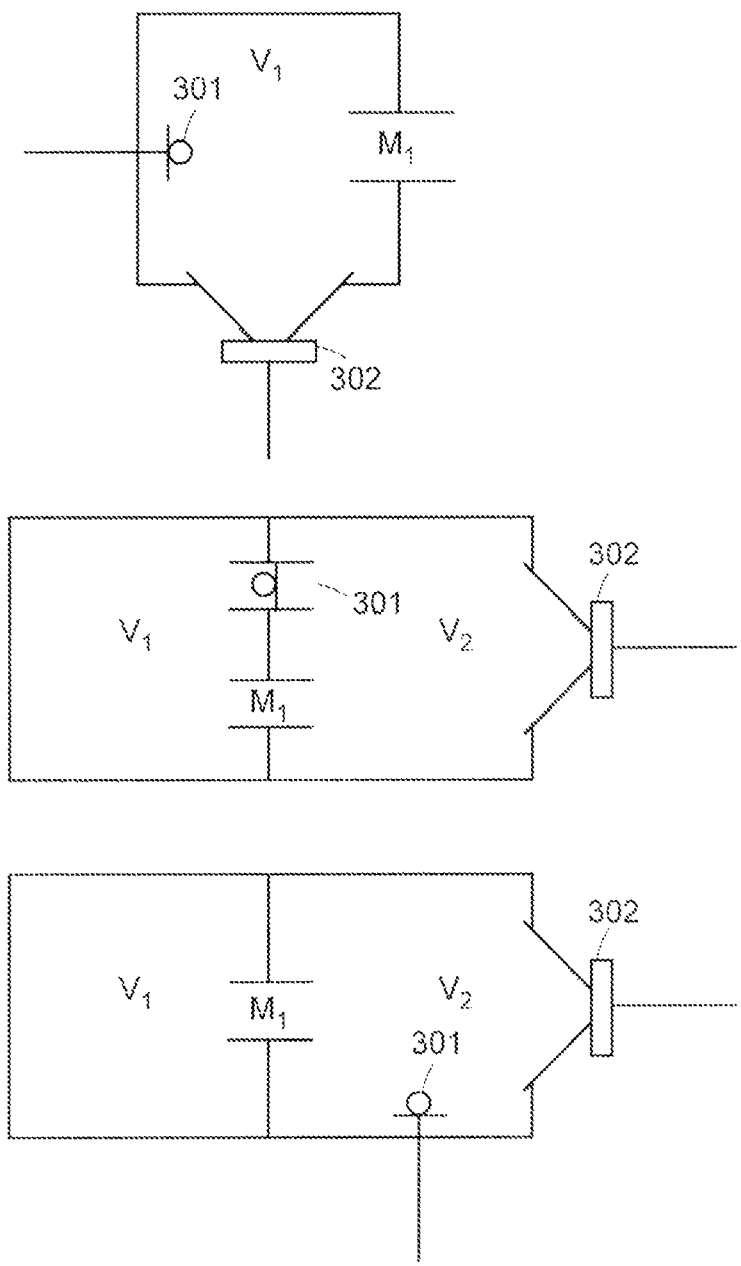
FIG. 3 is a schematic diagram of acoustic volume sensors that can be used with three embodiments of the invention.

Processor 204 is further coupled to power 206 to power the atomizer on and off at the appropriate time. FIG. 3 is a schematic diagram of acoustic volume sensors that can be used with three embodiments of the invention. In each embodiment, the chamber has volume V1, and is acoustically coupled to port M1 to form an acoustic system. Microphone 301 (or other suitable acousto-electrical transducer) and an acoustic source 302, such as a speaker, (or other suitable electro-acoustical transducer) are acoustically coupled to this acoustic system. The electrical output of the microphone is placed in communication with electrical input of acoustic source 302, in such a way that the amplitude and phase relationships of the signals promote acoustic resonance of the system. A measurement of a quantity related to the system's resonant frequency can permit determination of the chamber volume, as is described in U.S. Pat. No. 5,349,852, incorporated herein in its entirety. Such a resonance frequency measurement can be achieved in a processor. Alternatively, an additional chamber of known volume, configured with a port in a manner similar to one of the embodiments of FIG. 3, may be employed to produce a resonance, and a quantity related to the resonant frequency may be measured. This can, in turn, lead to a determination of the relevant volume.

In embodiment (1) of FIG. 3, microphone 301 is placed within the chamber, and acoustic source 302 forms a portion of the wall of the chamber. Because the resonance determination does not require that the chamber be sealed in the fashion required for acoustic-pressure type systems, the transducers employed in these embodiments do not need to be located in the chamber forming part of the system. It is necessary only that the transducers be acoustically coupled to the system.

In embodiments (2) and (3) of FIG. 3, a second volume V2 is associated with the system and is coupled to volume V1 via port M1. In each of embodiments (2) and (3), acoustic source 302 forms a portion of the wall of volume V2, and can be, for example, a piezoelectric speaker. In embodiment (2), microphone 301, which can be, for example, of the velocity type, forms a part of the wall between volumes V1 and V2, and responds only to differences in pressure between the two volumes; because the pressure difference between the two volumes tends to be near zero at frequencies below the frequency of natural resonance of the system, noise in microphone 301 is effectively canceled out. In embodiment (3), microphone 301 is disposed in volume V2.

Figure 4:
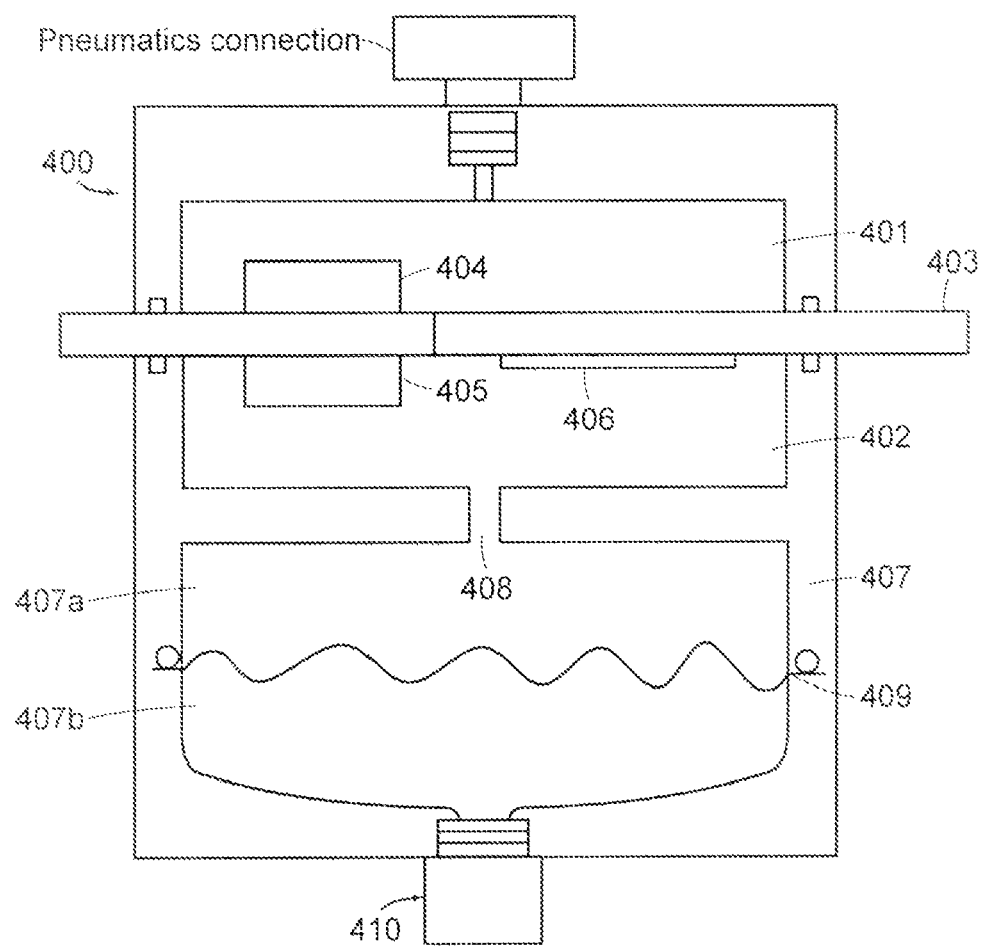
FIG. 4 is a schematic diagram of an acoustic volume sensor according to an embodiment of the invention.

FIG. 4 is a schematic diagram of an acoustic volume sensor according to an embodiment of the invention. In this embodiment, acoustic volume sensor enclosure 400 includes first volume 401 and second volume 402, separated by printed circuit board 403. First microphone 404 is acoustically coupled to first volume 401, and second microphone 405 is acoustically coupled to second volume 402.

Printed circuit board 403 contains an acoustic source, which can be, for example, a piezoelectric speaker. In one embodiment, one or both of first microphone 404 and second microphone 405 is attached to printed circuit board 403. Printed circuit board 403 can include, in one embodiment, an inner layer configured to pass electrical signals. Printed circuit board 403 is coupled to acoustic volume sensor enclosure 400 in a way that forms a substantially air-tight seal. In one embodiment, printed circuit board 403 includes a hole to equalize pressure between the first volume and the second volume. In this embodiment, the hole is small enough so as to not adversely impact the acoustic qualities of the system.

First microphone 404 and second microphone 405 are coupled to a processor (not shown). This processor is configured to receive a signal from the microphones, and is further configured to determine a volume of the variable-volume chamber based on the received signals. In one embodiment, the processor is contained on printed circuit board 403.

Second volume 402 is coupled to third volume 407 via port 408 in such a way as to create an acoustic system including second microphone 405 and acoustic source 406. Third volume 407 is divided into air portion 407a and fluid portion 407b. In one embodiment, third volume 407 is a detachable cassette. Air portion 407a can contain air, or can contain any suitable gas for creating an acoustic resonance for volume determination. Fluid portion 407b can include any fluid, including medicine, ink, or any fluid for which a volume measurement is desired. In one embodiment, air portion 407a is separated from fluid portion 407b by a diaphragm 409. Diaphragm 409 is configured to allow for a volume measurement of air portion 407a. Fluid portion 407b of third volume 407 includes fluid output fitting 410 for allowing fluid to escape from fluid volume 407b in a controlled way.

The basic theory behind the acoustic volume sensor according to an embodiment of the invention is that two chambers of air separated by a relatively small tube of air will resonate at a specific frequency when provided with an impulse to either of the air chambers or to the air in the tube that connects the chambers. The resultant resonant frequency is related to the volumes of the chambers, the tube dimensions and miscellaneous parameters of the gas that is used as a medium within the resonator.

To ensure a resonance exists as described by the basic theory, some assumptions may be used. First, the wavelength associated with the resonant frequency should be significantly larger than any of the critical dimensions of the resonator. Typically, the free-space wavelength associated with an acoustic wave of the resonant frequency should be approximately 20 times larger than the diameter of the chambers, and also of the length and diameter of the tube. This assumption provides that the air pressure within a given chamber is approximately uniform throughout the volume and that the air in the tube is also at a uniform pressure. Resonators having resonant frequencies with wavelengths less than 20 times the critical dimensions can be designed with acceptable behavior. The applicability of the assumptions, however, and the relevance of the theory will be diminished as the wavelength is decreased (or, conversely, the resonant frequency is increased) for a given resonator design.

Second, the energy lost from the resonator should be kept small so that the resonator will be underdamped. The resonator is modeled as a second-order system and the corresponding losses (damping) should be kept small so that the resonance can be readily observed. No widely accepted "rules of thumb" exist to determine the acceptability of various losses. Furthermore, no extensive studies have been performed to determine, without experimentation, the degree of losses that are expected for a given resonator geometry. Most of the losses are believed to be the result of viscous losses to the walls of the tube as the air traverses the tube's length.

Finally, at all frequencies of interest, the acoustic processes should be adiabatic. In other words, the acoustic processes should occur at a rate sufficient to keep heat energy from either leaving the system or equilibrating with the surrounding media. For the purposes of this document, acoustic processes at audible frequencies are always considered to be adiabatic.

Figure 5A:
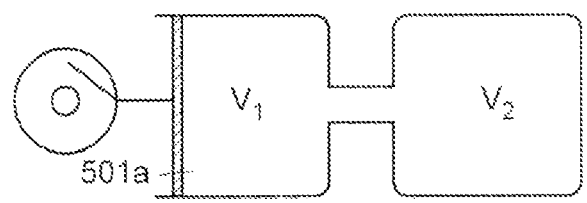
FIGS. 5A-5C is a schematic diagram of a number of acoustic volume sensors that further describe and explain embodiments of the invention.
Figure 5B:
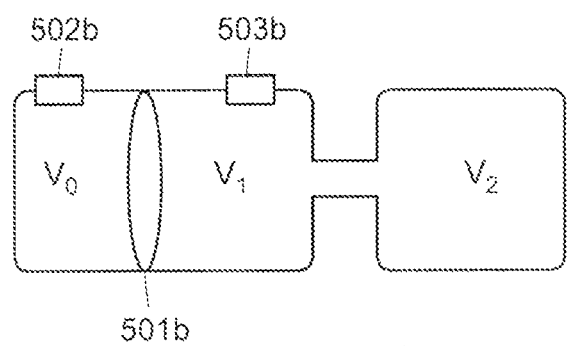
Figure 5C:
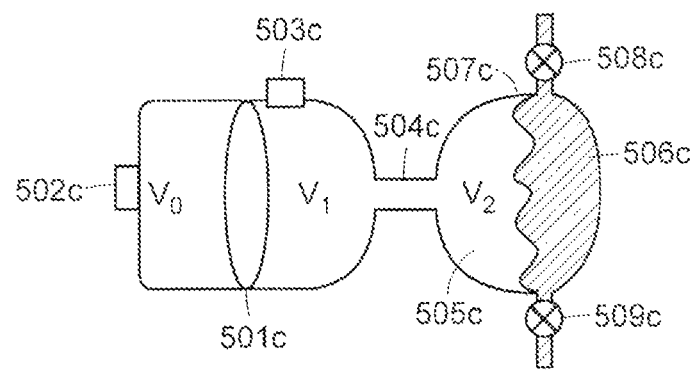

FIGS. 5A-5C is a schematic diagram of a number of acoustic volume sensors that further describe and explain embodiments of the invention. All of the following representations are considered equivalent with the only differences being required for practical implementation. FIG. 5a describes a simplified resonator using a piston 501a to vary the $V_1$ volume and excite the system. FIG. 5b replaces the piston with a speaker 501b for excitation and incorporates microphones 502b and 503b for determining the acoustic pressure levels present in the $V_0$ and $V_1$ volumes.

FIG. 5c depicts the implementation details required to utilize the resonator for measurement of volumes that vary as a result of fluid movements using a diaphragm as an interface and valves for control. In this figure, speaker 501c is used to excite the system, and microphones 502c and 503c for determining the acoustic pressure levels present in the $V_0$ and $V_1$ volumes.

Volume $V_2$ is acoustically coupled to volume $V_1$ via port 504c. Volume $V_2$ can be detachable from volume $V_1$ at port 504c. Volume $V_2$ includes gas region 505c and fluid region 506c. In one embodiment, fluid region 506c can be bounded by delivery input valve 508c and patient valve 509c. Delivery input valve 508c is configured to be coupled to a fluid source that allows fluid to flow into the volume for metering upon output. Patient valve 509c can be processor controlled to open and close to allow a specific volume of fluid to exit fluid region 506c.

The theoretical acoustic behavior can be modeled using a simple mechanical analog. Air volumes have frequency-dependent performance analogous to springs. Air ports have frequency-dependent performance analogous to masses. Acoustic dampers within air ports have an analogous effect on performance as a frictional surface over which a mass is forced to slide.

Figure 6:
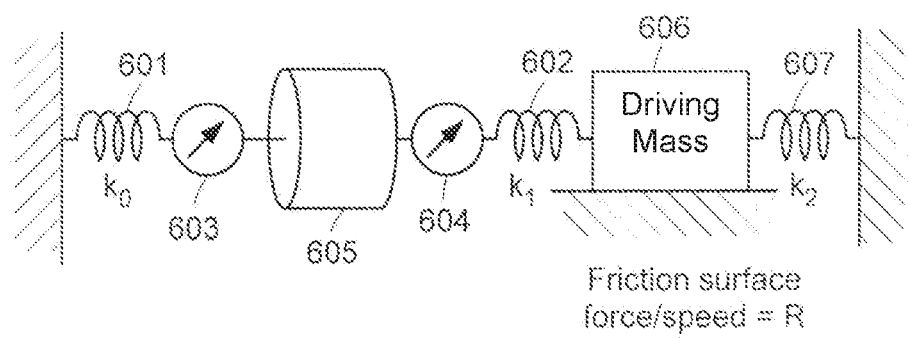
FIG. 6 is a schematic diagram of a mechanical analog to the system according to an embodiment of the invention.

FIG. 6 is a schematic diagram of a mechanical analog of an acoustic volume sensor according to an embodiment of the invention. In FIG. 6, to make the analogy explicit, spring 601 has a spring constant $K_0$ analogous to the volume $V_0$, spring 602 has a spring constant $K_1$ analogous to volume $V_1$, and spring 607 has a spring constant $K_2$ analogous to volume $V_2$. Reference force sensor 603 is analogous to the reference microphone, and front force sensor 604 is analogous to the front microphone. Piston 605 can excite the system in a way analogous to the speaker, driving mass 606 analogously to the air port.

Similarly, embodiments of the acoustic volume sensor can be modeled as an electrical circuit (not shown), with capacitors taking the place of springs (or volumes), a current source driving the system in place of the piston (or speaker), and inductors and resistors representing the mass (or port).

Figure 7:
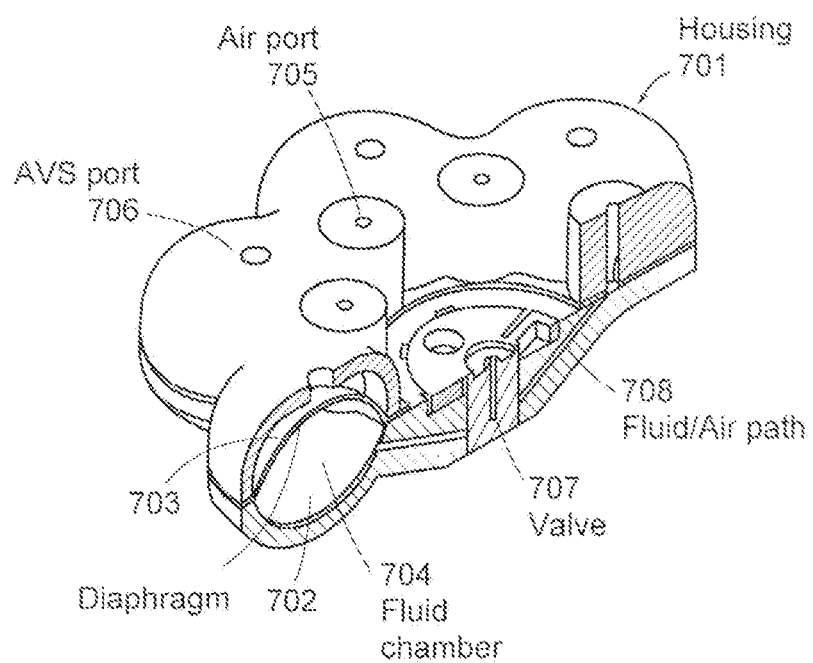
FIG. 7 is a cutaway view of a detachable cassette for which a volume determination can be made, according to an embodiment of the invention.

FIG. 7 is a cutaway view of a detachable cassette for which a volume determination can be made, according to an embodiment of the invention. In this embodiment, housing 701 contains selectable volume 702, which is divided into air chamber 703 and fluid chamber 704. Air chamber 703 and fluid chamber 704 are, in one embodiment, separated by a diaphragm.

Housing 701 includes air port 705 for coupling to an air source such as a condensed air source. Housing 701 further includes AVS port 706 for acoustically coupling volume 702 to an acoustic volume sensor.

In one embodiment, housing 701 can contain multiple selectable volumes 702, each with a corresponding AVS port 706, air port 705, valve 707 and fluid/air path 708. In one embodiment, one selectable volume 702 can share an AVS port 706, an air port 705, a valve 707 and a fluid/air path 708 with another selectable volume 702. Each selectable volume 702 is configured to be individually selectable for acoustic coupling with an acoustic volume sensor.

In one embodiment, fluid chamber 704 is coupled to valve 707 by fluid/air path 708 for outputting a selected amount of fluid from fluid chamber 704, based on a volume determined in air chamber 703. Fluid/air path 708 is further configured to be coupled to an air source for purging parts of the system.

In one embodiment, valve 707 is configured to be coupled to fluid chamber 704 when fluid chamber 704 is coupled to an acoustic volume sensor. Valve 707 is further configured to be coupled to a processor (not shown), and configured to receive a control signal from the processor to open and close based on a volume determined in air chamber 703. Valve 707 is configured to be coupled to an atomizer.

Figure 8:
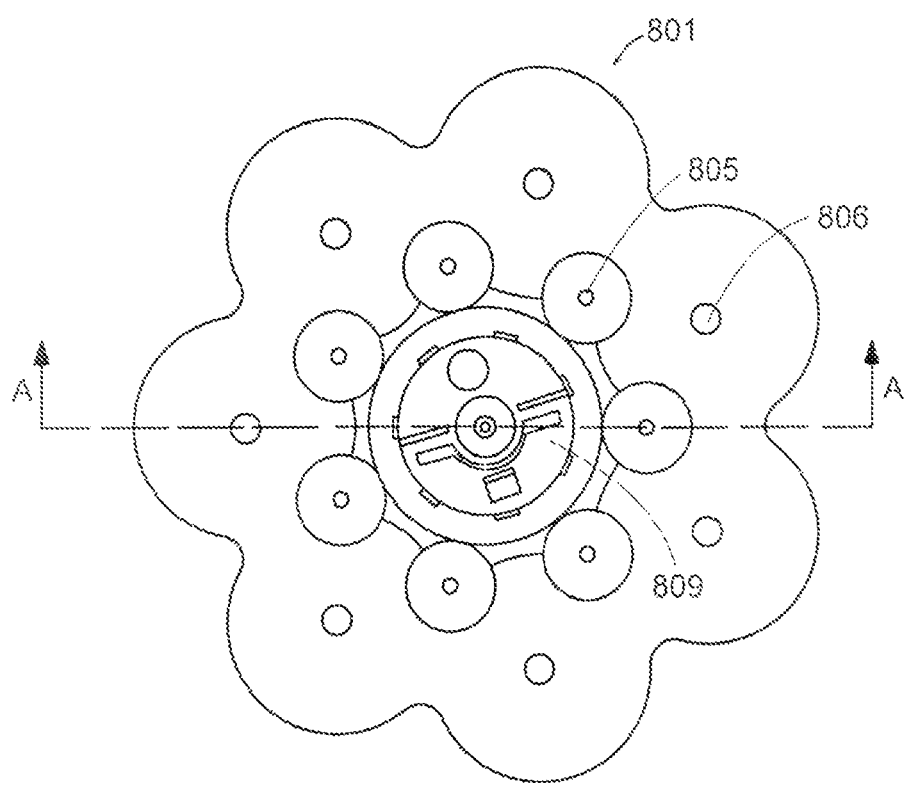
FIG. 8 is a top view of a detachable cassette for which a volume determination can be made, according to an embodiment of the invention.

FIG. 8 is a top view of a detachable cassette for which a volume determination can be made, according to an embodiment of the invention. In this embodiment, the detachable cassette includes 7 selectable volumes, which can be seen from the corresponding air ports 805 and acoustic volume sensor ports 806. In principle, housing 801 can include any practicable number of selectable volumes.

Valve 807 can be seen attached to acoustic volume sensor coupling 809. Acoustic volume sensor coupling 809 is configured to detachably couple the detachable cassette to a fluid volume sensor in a way that allows any selectable volume to be selectably coupled to an acoustic volume sensor.

Figure 9:
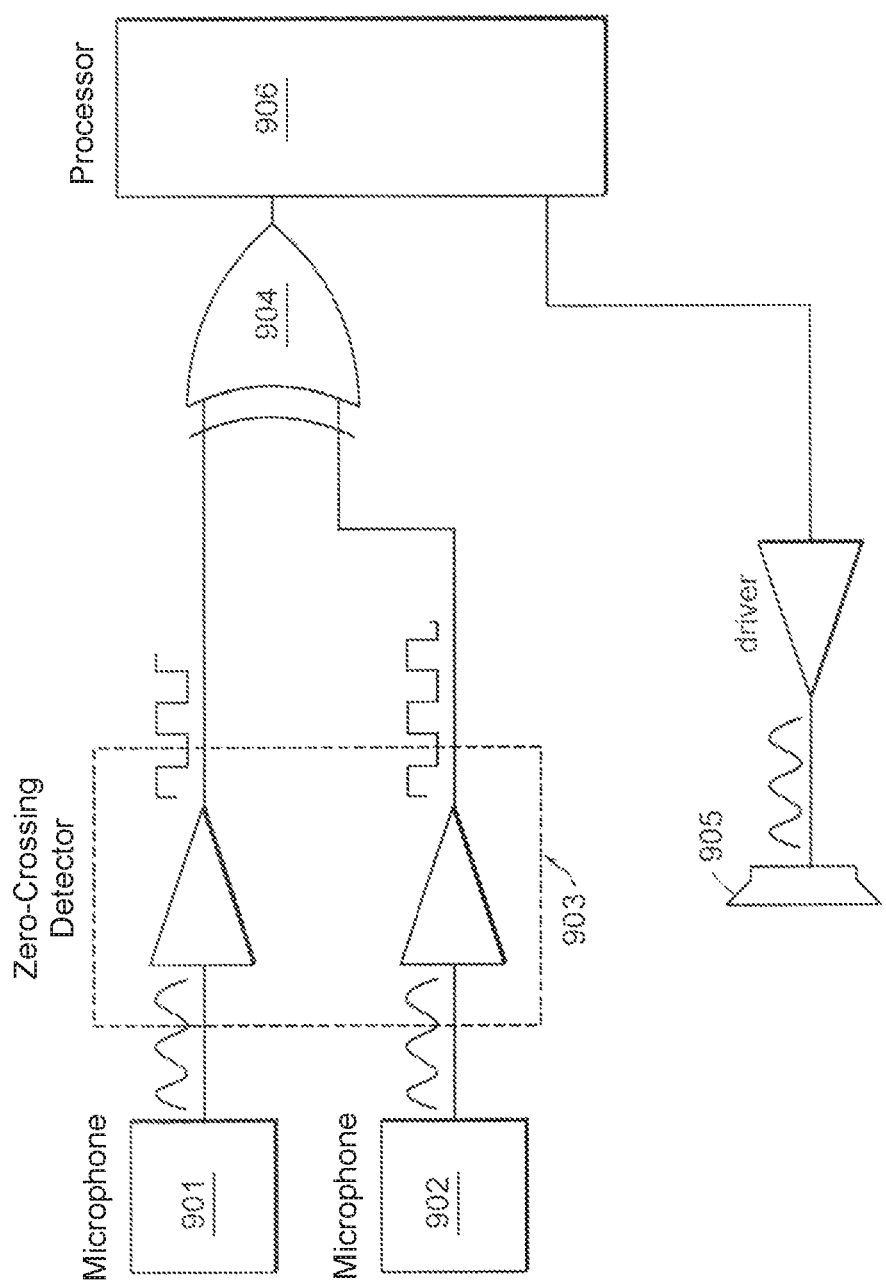
FIG. 9 is a schematic diagram of a signal processing technique according to an embodiment of the invention.

Acoustic volume sensors can employ a number of signal processing techniques to determine the resonance and volume of a variable volume chamber. FIGS. 9-23 illustrate several exemplary methods of signal processing. In FIG. 9, a speaker is driven with a fixed frequency sinusoid and the phase difference between microphones 901 and 902 is measured. In this embodiment, the microphone outputs are passed through zero-crossing detector 903 to create digital square waves in phase with their analog sine outputs. The two square waves are then passed through an exclusive OR gate, XOR 904; the duty cycle of the XOR 904 output, which is proportional to the phase difference, is measured. After determining the phase difference, a different frequency is output from speaker 905, and the new phase difference is measured. This is repeated until the system finds the frequencies for which the phase difference straddles 90 degrees. Linear interpolation can then be used to calculate the system's resonant frequency. Phase difference is measured, and the system is controlled, by processor 906.

Figure 10:
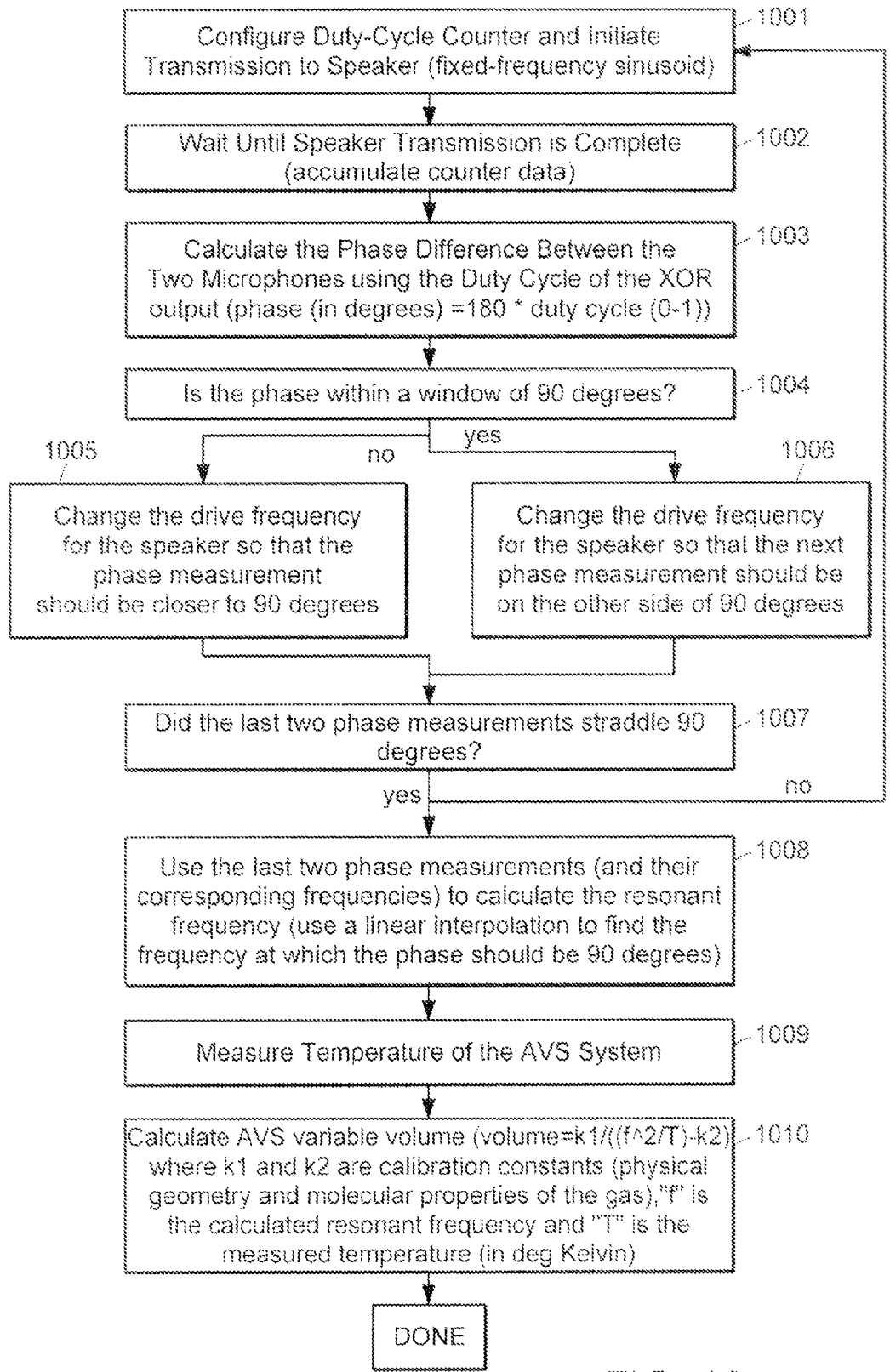
FIG. 10 is a flow chart of the signal processing technique illustrated in FIG. 9.

FIG. 10 is a flow chart describing the steps of acoustic volume sensing using the digital duty-cycle technique illustrated in FIG. 9. In one embodiment, at step 1001, a duty-cycle counter is configured, and transmission to a speaker is initiated. The speaker is configured in this embodiment to output a fixed frequency sinusoidal signal.

At step 1002, counter data is accumulated as the speaker transmission is completed. The phase difference between the two microphones, at step 1003, is then calculated using the duty cycle of the XOR output using the equation phase (in degrees)=180*duty cycle(0-1).

Once the phase difference is determined, then at step 1004, a determination is made as to whether the phase difference is within some predetermined window of 90 degrees. If not, then at step 1005, the drive frequency is changed to move the phase measurement closer to 90 degrees. If the phase difference is within some predetermined window of 90 degrees, then at step 1006, the speaker drive frequency is changed so that the next phase measurement is on the other side of 90 degrees.

At step 1007, a determination is made as to whether the last two phase measurements straddle 90 degrees. If not, the system is reset back to step 1001. If so, then the last two phase measurements (and their corresponding frequencies) are used to calculate the resonant frequency, using a linear interpolation to find the frequency at which the phase difference is 90 degrees.

At step 1009, the temperature of the system is measured. Using the known variables, the relevant volume is measured using the equation (volume=k1/((f^2/T)−k2), where k1 and k2 are calibration constants (e.g., the physical geometry and molecular properties of the gas), "f" is the calculated resonant frequency, and "T" is the measured temperature in degrees Kelvin.

Figure 11:
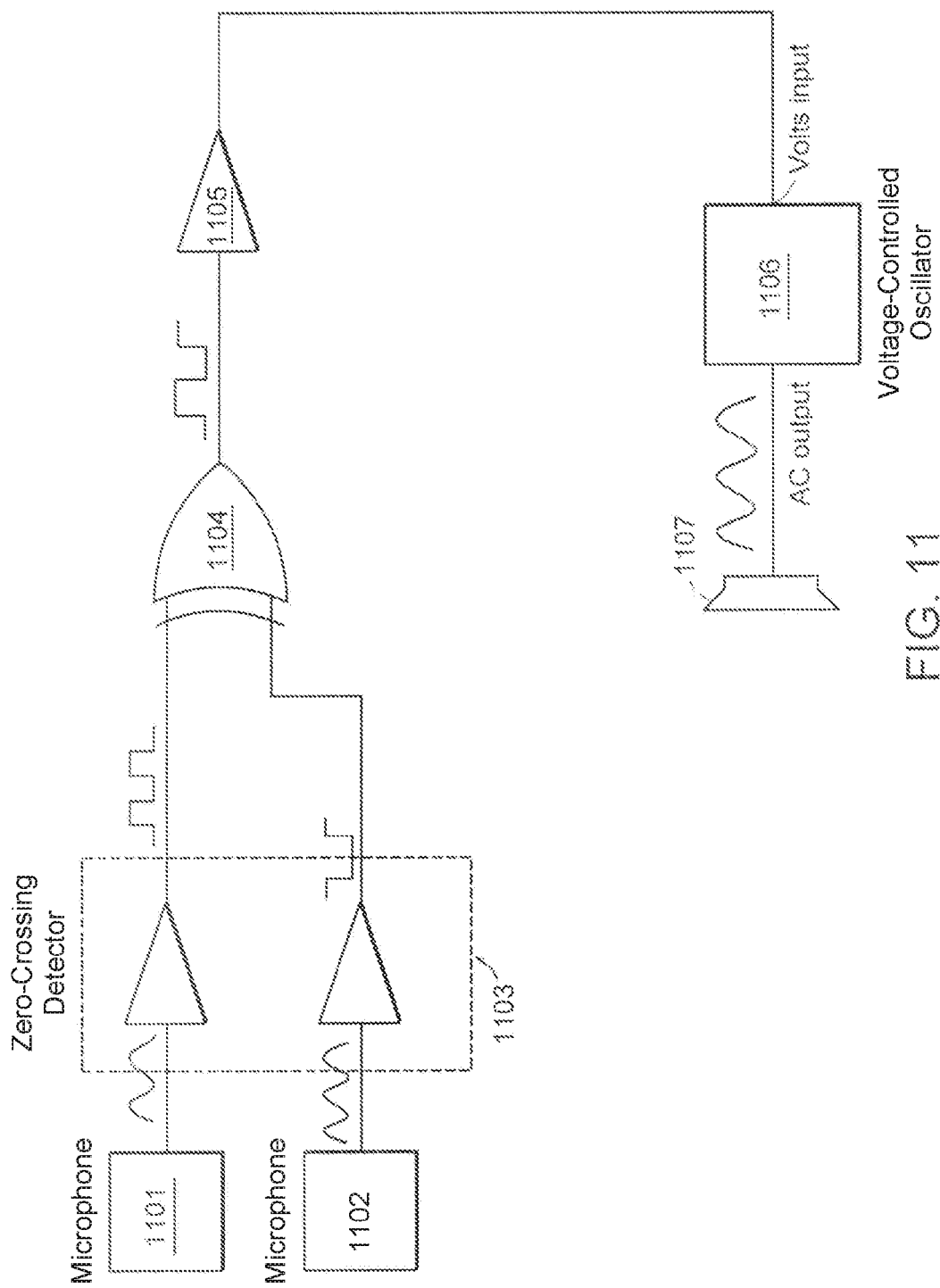
FIG. 11 is a schematic diagram of a signal processing technique according to an embodiment of the invention.

FIG. 11 is a schematic diagram of signal processing techniques according to an embodiment of the invention. The technique illustrated is similar to the technique displayed in FIG. 9, except that a voltage-controlled oscillator, or VCO 1106, is used instead of a processor to generate speaker drive signals, with VCO 1106 input driven by the output from XOR 1104 and then passed through integrator 1105. In principle, this circuit will automatically find the system's resonant frequency by locking onto the 90 degree phase difference. The integrator output is only stationary with 50% of the XOR 1104 output duty cycle. The VCO input and output is then altered to maintain a 50% XOR duty cycle. With this technique, an external processor (not shown) can either measure the input voltage to VCO 1106 (with voltage being substantially proportional to frequency), or can measure the frequency of the signal driving speaker 1107, or can measure the frequencies of microphones 1101 and 1102, or can measure the output from XOR 1104.

Figure 12:
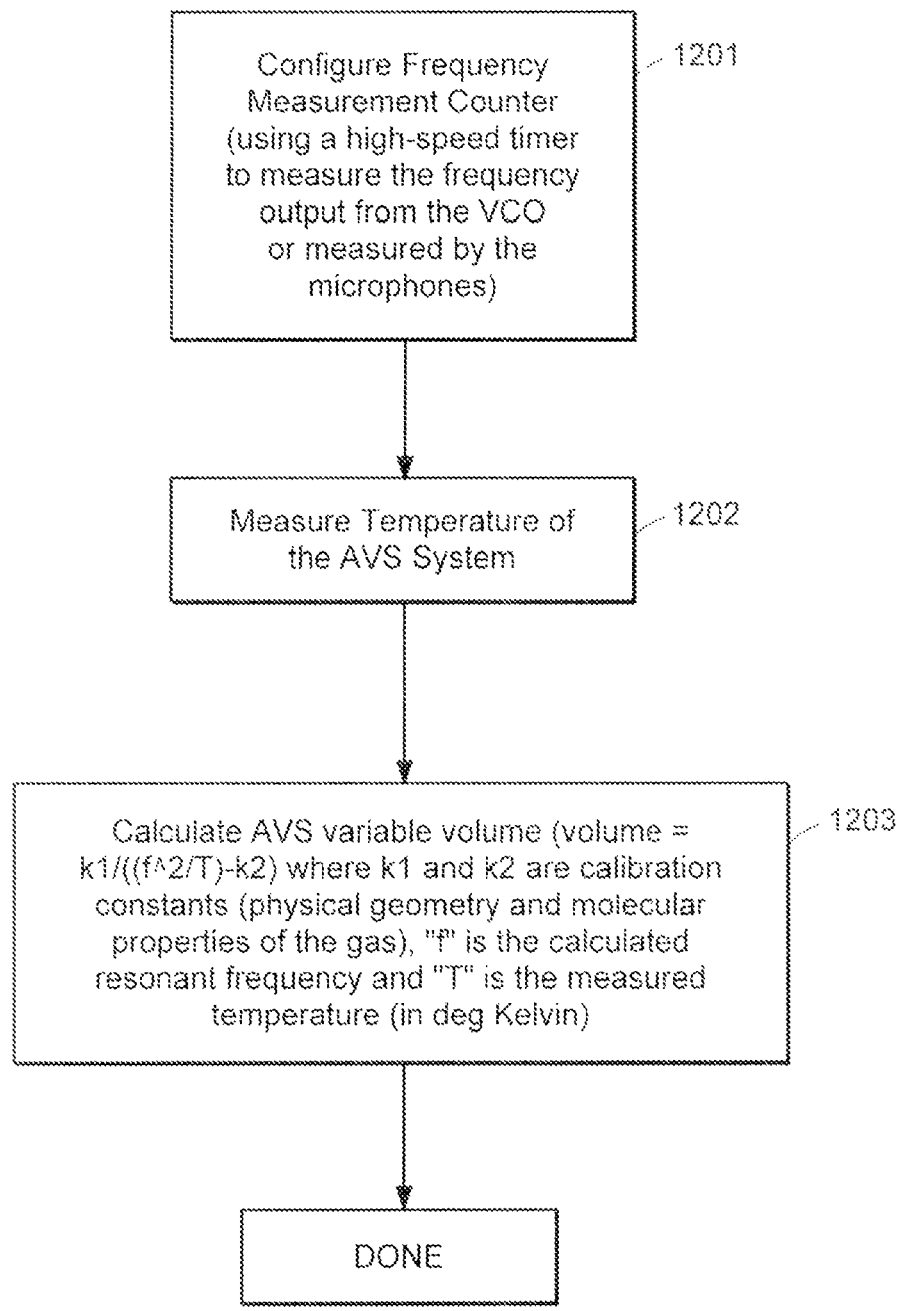
FIG. 12 is a flow chart of the signal processing technique illustrated in FIG. 11.

FIG. 12 is a flow chart of the signal processing technique illustrated in FIG. 11, according to an embodiment of the invention. In this embodiment, at step 1201, a frequency measurement counter is configured, possibly using a high-speed timer to measure the frequency output from the VCO, or measured by the microphones.

At step 1202 the temperature of the system is measured. Using this information, the volume is calculated using the equation (volume=k1/((f^2/T)−k2), where k1 and k2 are calibration constants (e.g., the physical geometry and molecular properties of the gas), "f" is the calculated resonant frequency, and "T" is the measured temperature in degrees Kelvin.

Figure 13:
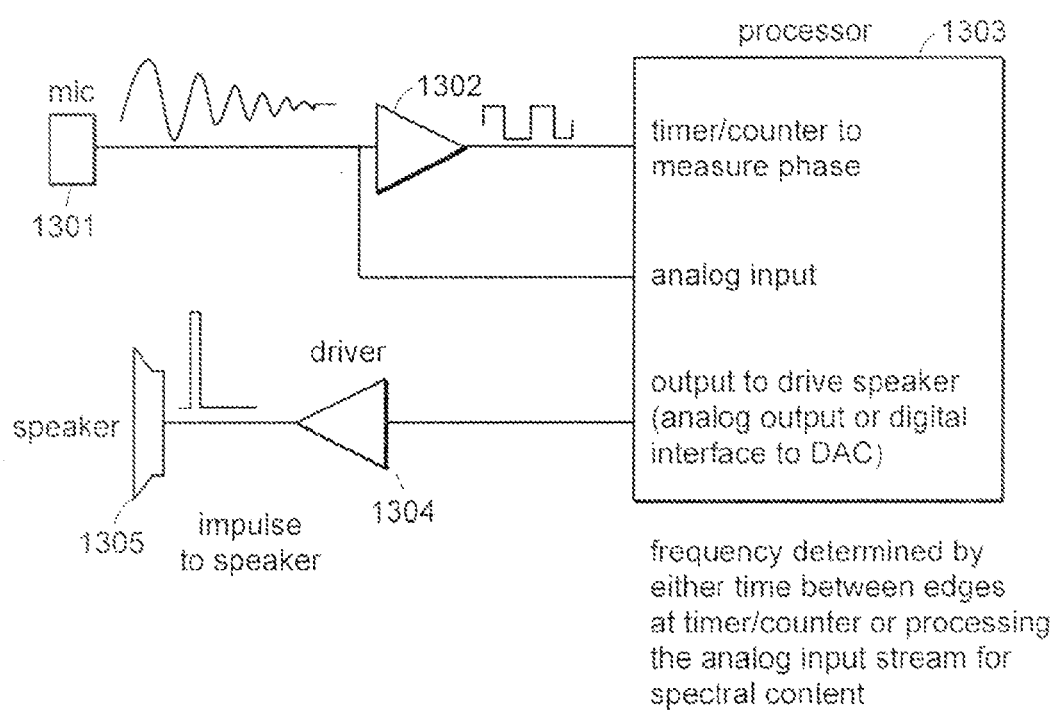
FIG. 13 is a schematic diagram of a signal processing technique using a speaker impulse, according to an embodiment of the invention.

FIG. 13 is a schematic diagram of a signal processing technique using a speaker impulse, according to an embodiment of the invention. In this embodiment, driver 1304 applies an impulse to speaker 1305. The microphone output from microphone 1301 will deliver a resonant response to processor 1303. The frequency can, in principle, be determined by either time between the edges at the timer/counter, or by processing the analog input stream for spectral content. This embodiment would, in theory, eliminate the reference microphone. In a related embodiment, if the speaker dynamics are well behaved, the reference microphone can, in theory, be eliminated; the phase difference between the microphone's output and the speaker drive signals can be measured instead.

Figure 14:
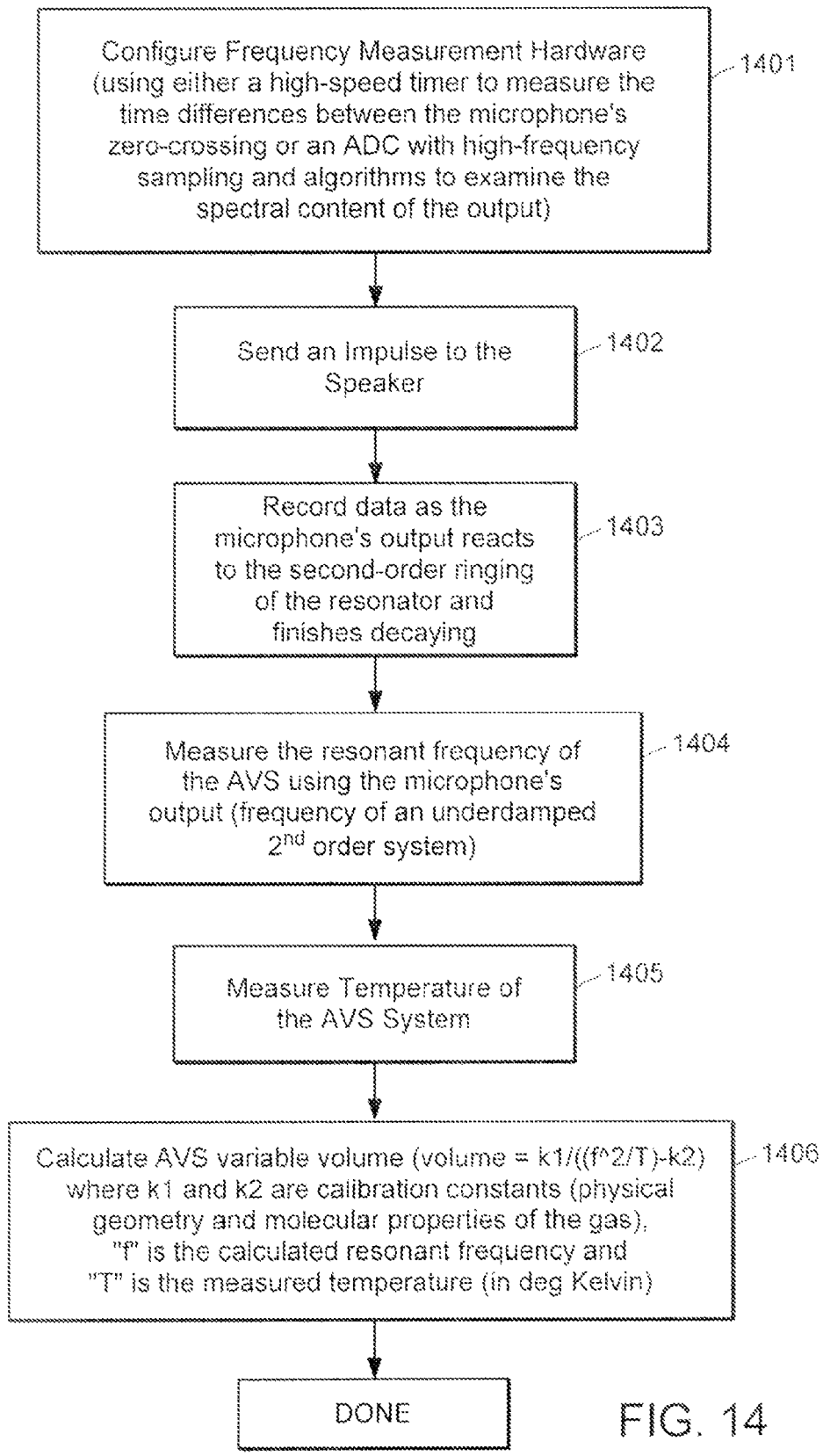
FIG. 14 is a flow chart of the signal processing technique illustrated in FIG. 13.

FIG. 14 is a flow chart of the signal processing technique illustrated in FIG. 13. At step 1401, the frequency measurement hardware is configured. This can be performed using either a high-speed timer to measure the time differences between the microphone's zero crossing, or by using an analog to digital converter using high-frequency sampling and algorithms to examine the spectral content of the output.

At step 1402, an impulse is sent to the speaker. At step 1403, data is recorded as the microphone's output reacts to the second-order ringing of the resonator and finishes decaying. The resonant frequency is measured at step 1404 using the microphone's output. The frequency is associated with the underdamped second-order system.

The temperature is then measured at step 1405, and at step 1406, the relevant volume is then calculated using the equation (volume=k1/((f^2/T)−k2), where k1 and k2 are calibration constants (e.g., the physical geometry and molecular properties of the gas), "f" is the calculated resonant frequency, and "T" is the measured temperature in degrees Kelvin.

The signal processing techniques described above can be performed using amplitude ratios instead of resonances. This technique does not specifically require the presence of an acoustic port, although with standard electronics, amplitude measurements typically lack the accuracy and precision of phase measurements. With newer, higher performance analog to digital converters and digital signal processors, amplitude ratio measurements can be an accurate substitute.

Figure 15:
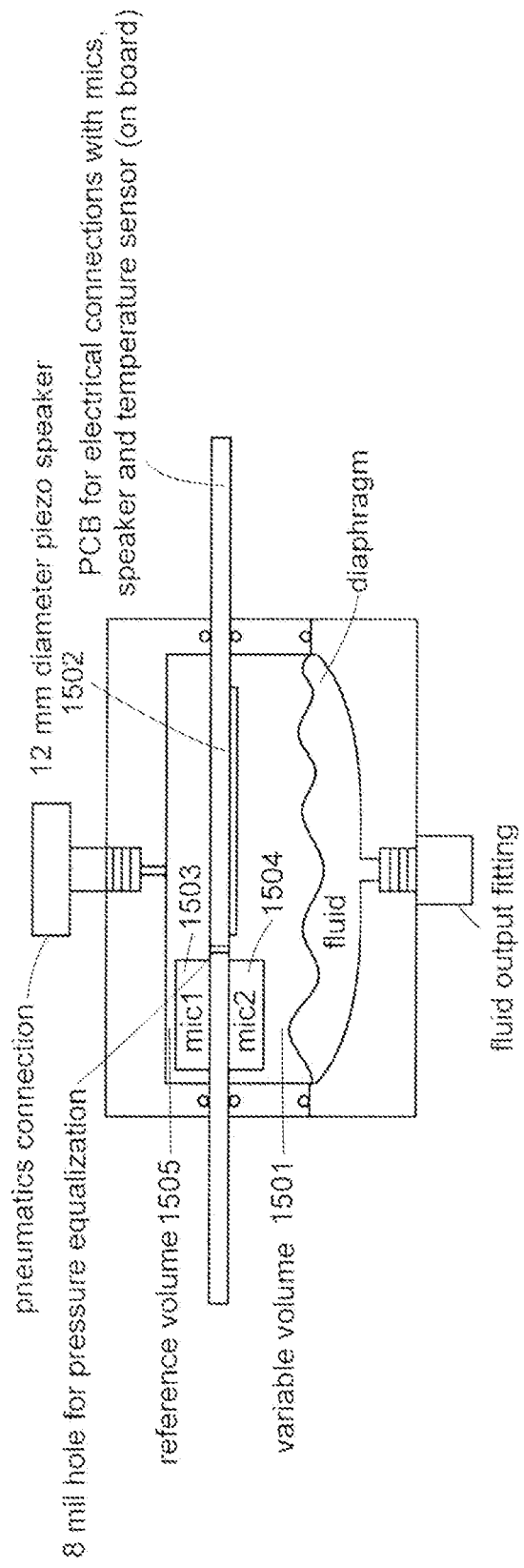
FIG. 15 is a schematic diagram of an embodiment of the invention that does not require the presence of an acoustic port.
Figure 16:
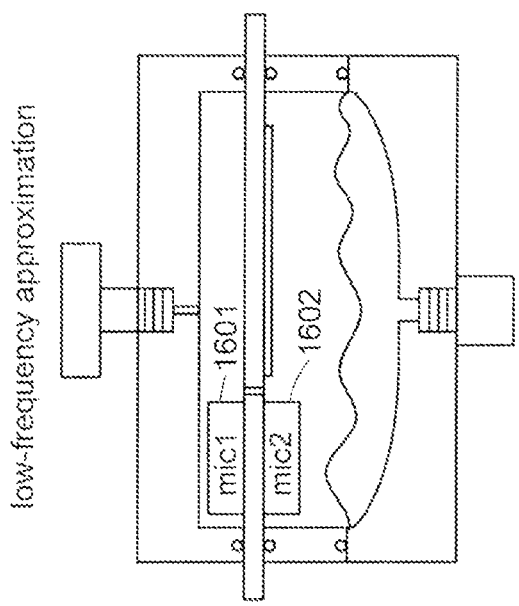
FIG. 16 is a schematic diagram of a low-frequency approximation of an acoustic volume sensor, according to an embodiment of the invention.

FIG. 15 is an embodiment of the invention that does not require the presence of an acoustic port. Variable volume 1501 can be measured by driving the speaker sinusoidally and measuring the ratio of the amplitudes at microphone 1503 and microphone 1504. Given that the speaker is a displacement device, the pressure increase in the variable volume will be proportional to the pressure decrease in reference volume 1505. When reference volume 1505 and variable volume 1501 are equal, both microphones output the same signal level and are 180 degrees out of phase (assuming identical microphones). If the variable volume is one half the size of the reference volume, the output from microphone 1504 is twice that of microphone since, for the same speaker displacement, the acoustic pressure change in variable volume 1501 (as a portion of its nominal value) is twice as large as the change in the reference volume. The relationship is true as long as the drive frequency for the speaker produces an acoustic wavelength much longer than any of the volumes' dimensions.

The above amplitude ratio technique is also useful when implementing an acoustic volume sensor with an acoustic port. At frequencies much less than the resonances of the system, the acoustic port becomes effectively transparent (as in FIG. 16), and the "fixed" and "variable" volumes cannot be distinguished. This embodiment can be considered a low-frequency approximation of acoustic volume sensing.

Figure 17:
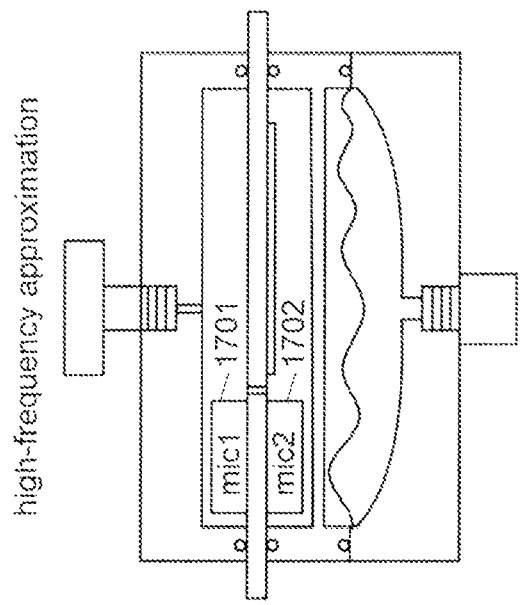
FIG. 17 is a schematic diagram of a high-frequency approximation of an acoustic volume sensor, according to an embodiment of the invention.

At frequencies much higher than the system resonances, the acoustic port's impedance becomes significant and no acoustic energy passes from the port into the variable volume, as is shown in FIG. 17. At such frequencies, the ratio of the amplitudes between microphone 1701 and 1702 is fixed, and is independent of the variable volume (ratio=reference volume/fixed volume).

Figure 18:
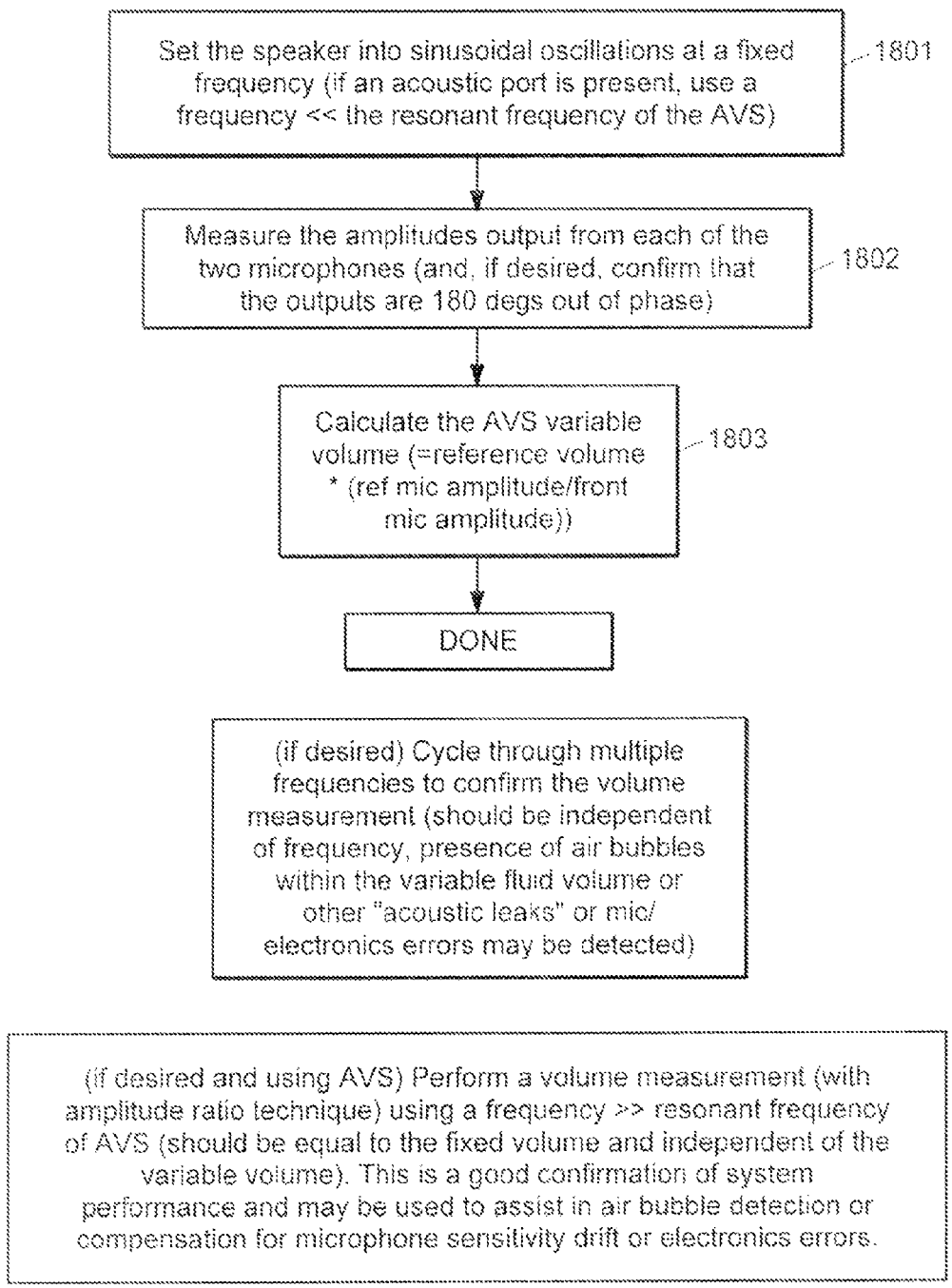
FIG. 18 is a flow chart of a signal processing technique using amplitude ratio measurements, according to an embodiment of the invention.

FIG. 18 is a flow chart of a signal processing technique using amplitude ratio measurements, according to an embodiment of the invention. In this embodiment, at step 1801, the speaker is set into sinusoidal oscillations at a fixed frequency. If an acoustic port is present, the frequency used can be much less than the resonant frequency of the acoustic volume sensor.

At step 1802, the amplitudes output from the two microphones are measured. If desired, the phase of the two outputs can be confirmed to be 180 degrees out of phase. At step 1803, the variable volume is calculated using the equation volume=reference volume*(reference microphone amplitude/front microphone amplitude).

If desired, one can cycle through multiple frequencies to confirm the volume measurement. The measurement should be independent of frequency, the presence of air bubbles within the variable fluid volume, or other "acoustic leaks" or microphone or electronics errors that may be detected.

If desired, using an amplitude ratio technique, a volume measurement may be performed using a frequency much larger than the resonant frequency of the system. The volume measurement in this case should be approximately equal to the fixed volume and approximately independent of the variable volume.

The foregoing description of the embodiments of the invention has been presented only for the purpose of illustration and description and is not intended to be exhaustive or to limit the invention to the precise forms disclosed. Numerous modifications and adaptations thereof will be apparent to those skilled in the art without departing from the spirit and scope of the present invention.

What is claimed is:

1. An apparatus for determining the fluid volume output from a fluid region, the apparatus comprising:
    a housing containing a first volume and a second volume, the second volume including an air region, the air region containing an air volume and a fluid region containing a fluid volume, the first volume and the air region form at least part of an acoustic system;
    a printed circuit board disposed within the housing, the printed circuit board defining the first volume within the housing and the printed circuit board including:
        an acoustic source acoustically exciting the acoustic system,
        a first microphone acoustically coupled to the first volume, the first microphone producing a first signal based on a response of the first volume to excitement by the acoustic source, and
        a second microphone acoustically coupled to the air region, the second microphone producing a first signal based on a response of the air region to excitement by the acoustic source;
    a processor in communication with the acoustic source, the first microphone and the second microphone, the processor comprising:
    determining a first air volume associated with the first signal and second signal at a first instance,
    determining a second air volume associated with the first signal and second signal at a second instance,
    determining the fluid volume output from a fluid region associated with the difference between the first air volume and the second air volume.

2. The apparatus of claim 1, wherein the printed circuit board comprising the processor.

3. The apparatus of claim 1, wherein at least one of the first microphone and the second microphone is attached to the printed circuit board.

4. The apparatus of claim 1, wherein the air region is separated from the fluid region by a diaphragm, and wherein the air region and the fluid region form a fixed volume.

5. The apparatus of claim 4, further comprising a detachable cassette defining the fluid region of the second volume.

6. The apparatus of claim 1, wherein the housing further comprises a valve, the valve is in fluid communication with the fluid region.

7. The apparatus of claim 6, wherein the processor comprises:
    driving the acoustic source at fixed frequency;
    receiving a first signal from the first microphone;
    receiving a second signal from the second microphone; and
    outputting a control signal to the valve, the control signal being associated with the first signal and the second signal.

8. The apparatus of claim 7, wherein the control signal comprises information associated with releasing the fluid volume.

9. The apparatus of claim 1, wherein the printed circuit board comprises a hole for pressure equalization between the first volume and the second volume.

10. The apparatus of claim 1, wherein the acoustic source comprises a piezoelectric speaker.

11. The apparatus of claim 1, wherein the printed circuit board forms an air-tight seal with the housing.

12. The apparatus of claim 1, wherein the printed circuit board further comprises a temperature sensor, the temperature sensor being in communication with the processor.

13. An apparatus for determining the chamber volume of a variable-volume chamber, the apparatus comprising:
    a housing including are fixed volume and the variable-volume chamber, the variable-volume chamber having a chamber volume, the variable-volume chamber being defined at least in part by the housing, the variable-volume chamber and fixed volume form at least part of an acoustic system;
    an acoustic source exciting the acoustic system;
    a printed circuit board disposed within the housing, the printed circuit board defining the fixed volume within the housing, the printed circuit board including:
        a first microphone acoustically coupled to the fixed volume, the first microphone producing a first signal associated with a acoustic response of the fixed volume to excitement by the acoustic source,
        a second microphone acoustically coupled to the variable-volume chamber, the second microphone producing a second signal associated with an acoustic response of the variable-volume chamber to excitement by the acoustic source; and
    a processor including:
        driving the acoustic source,
        receiving the first signal and the second signal, and
        determining the chamber volume associated with the first signal and second signal.

14. The apparatus of claim 13, wherein the printed circuit board separates the fixed volume from the variable-volume chamber.

15. The apparatus of claim 13, wherein the processor comprises determining the chamber volume associated with a resonant frequency of the acoustic system.

16. The apparatus of claim 13, wherein either of the first microphone or the second microphone is attached to the printed circuit board.

17. The apparatus of claim 13, wherein the printed circuit board forms an air-tight seal with the housing.

18. The apparatus of claim 13, wherein the printed circuit board further comprises a temperature sensor, the temperature sensor being in communication with the processor.

19. The apparatus of claim 18, wherein the processor comprises:
    receiving a third signal from the temperature sensor, and
    determining the chamber volume associated with the first signal, second signal and third signal.

20. The apparatus of claim 13, wherein the acoustic source comprises a piezoelectric speaker.

21. The apparatus claim 13, further comprising a detachable cassette mounted to the housing, the detachable cassette comprising a fluid region that is separated from the variable-volume chamber by a diaphragm.

22. The apparatus of claim 21, wherein the variable-volume chamber and the fluid region form a constant volume.

23. The apparatus of claim 21 further comprising a valve in communication with the fluid region.

24. The apparatus of claim 23, wherein the valve is in communication with the processor.

25. The apparatus of claim 24, wherein the processor outputs a control signal to the valve, the control signal being associated with the chamber volume.

26. The apparatus of claim 25, wherein the control signal comprises information associated with releasing a fluid volume from the fluid region.

27. An apparatus to control the flow of liquid, the apparatus comprising:
   a housing containing a valve, a first volume and a second volume, the second volume including a gas region, the gas region containing a gas volume and a liquid region containing a liquid volume, the valve being in fluid communication with the liquid region, the first volume and gas-region form at least part of an acoustic system;
   an acoustic source exciting the acoustic system;
   a printed circuit board disposed within the housing, the printed circuit board and housing defining the first volume and the printed circuit board including:
      a first microphone acoustically coupled to the first volume, the first microphone producing a first signal associated with a response of the first volume to excitement by the acoustic source, and
      a second microphone acoustically coupled to the gas region, the second microphone producing a first signal associated with a response of the gas region to excitement by the acoustic source; and
   a processor including:
      driving the acoustic source;
      receiving the first signal,
      receiving the second signal,
         determining the gas volume associated with the first signal and second signal, and
         controlling the valve to allow a liquid volume to exit the liquid region based on the gas volume.

28. The apparatus of claim 27, wherein the processor is arranged to determine the gas volume associated with a resonant frequency of the acoustic system.

29. The apparatus of claim 27, wherein the processor is arranged to determine a resonant frequency of the acoustic system based on an underdamped second-order model of the acoustic system.

30. The apparatus of claim 27, wherein the printed circuit board comprises the processor.

31. The apparatus of claim 27, wherein the gas region is separated from the liquid region by a diaphragm, and the gas region and the liquid region form a constant volume.

32. The apparatus of claim 27, wherein the control signal comprises information associated with releasing a volume of liquid.

33. The apparatus of claim 27, wherein the printed circuit board includes a hole for pressure equalization between the first volume and the second volume.

34. The apparatus of claim 27, wherein the acoustic source comprises a piezoelectric speaker.

35. The apparatus of claim 27, wherein the printed circuit board comprises a temperature sensor.

36. The apparatus of claim 35, wherein the processor comprises:
   receiving a third signal from the temperature sensor, and
   calculating the gas volume of the gas-region based on the received first signal, second signal and third signal.

* * * * *